US00PP32301P2

(12) United States Plant Patent
Slaughter

(10) Patent No.: US PP32,301 P2
(45) Date of Patent: Oct. 13, 2020

(54) ALMOND TREE NAMED 'BURALMONDTHREE'

(50) Latin Name: *Prunus dulcis*
Varietal Denomination: Buralmondthree

(71) Applicant: The Burchell Nursery, Inc., Oakdale, CA (US)

(72) Inventor: John K. Slaughter, Fresno, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 16/501,353

(22) Filed: Mar. 29, 2019

(51) Int. Cl.
*A01H 5/08* (2018.01)
*A01H 6/74* (2018.01)

(52) U.S. Cl.
USPC ..... Plt./155
CPC ..... *A01H 6/7427* (2018.05)

(58) Field of Classification Search
USPC ..... Plt./155
CPC ..... A01H 6/7427; A01H 5/08
See application file for complete search history.

*Primary Examiner* — Keith O. Robinson
(74) *Attorney, Agent, or Firm* — Randall Danskin P.S.

(57) ABSTRACT

A new and distinct variety of almond tree (*Prunus dulcis*), which is denominated varietally as 'Buralmondthree', and which exhibits self-fertility, high productivity, very high quality nuts, a firm and durable and well-sealed suture that results in reduced damage by some of the common insect pests in almonds, increased resistance to *Rhizopus stollinifer*, and produces almonds which are mature for harvesting and shipment approximately August 15th to August 25th under the ecological conditions prevailing in the San Joaquin Valley of Central California.

2 Drawing Sheets

Botanical designation: The present invention relates to a new, novel, and distinct variety of almond tree, '*Prunus dulcis*'.

Varietal denomination: 'Buralmondthree'.

BACKGROUND OF THE NEW VARIETY

The present variety of almond tree resulted from an on-going program of fruit and nut tree breeding. The purpose of this program is to improve the commercial quality of deciduous fruit and nut varieties, and rootstocks, by creating and releasing promising scion and rootstock selections of *Prunus, Malus, Punica* and *Juglans* species. To this end we make both controlled and hybrid cross pollinations each year in order to produce seedling populations from which improved progenies are evaluated and selected. After close field observation, one almond seedling, 'Buralmondthree' bred by us, was selected from the populations which are were planted in our experimental orchards near Fowler, Calif.

Prior Varieties. The listing of pre-existing almond varieties here is for purpose of comparison, source of parentage and reference and include: 'Nonpareil', (unpatented, self-incompatible variety bred by A. T. Hatch 1879, Suisun, Calif.); 'Tuono' Almond tree (an ancient landrace self-fertile, variety from the Puglia region of Southeastern Italy, commercially planted in Spain); the Monterey Almond tree (U.S. Plant Pat. No. 3,483, patent expired); and the 'B1.005' almond (unpatented).

Origin of the Variety. The seedlings, grown on their own roots, were derived from a cross, made in February 2001 using the 'Tuono' (nonpatented) almond tree, and which was used as the seed parent; and the Monterey Almond Tree (U.S. Plant Pat. No. 3,483 expired), and was used as the pollen parent. After fruit ripening, seed collection, and a period of stratification, the seed was germinated, grown in our greenhouses. The resulting seedlings were then field planted by population for tree establishment, and ultimately to express potential tree and nut phenology for evaluation. One self-fertile seedling, which is the present variety, exhibited especially desirable characteristics, and was then designated as 'P14.095'. This seedling was marked for subsequent observation. After the 2004 fruiting season, the new variety of almond tree was selected for advanced evaluation and repropagation.

ASEXUAL REPRODUCTION

Asexual reproduction of this new and distinct variety of almond tree was accomplished by budding (bud grafting) the new almond tree onto 'Nemaguard' Rootstock (un-patented). This was performed by us in our experimental orchard which is located near Fowler, Calif. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF VARIETY

'Buralmondthree' is a new and distinct variety of almond tree, which is considered of medium size, and which has a moderately vigorous and upright growth characteristic. This new tree is also a regular and productive bearer of relatively large, very light colored nuts which have a very good flavor, and is productive. This new almond tree has a medium-low chilling requirement of approximately 350 hours, and further produces relatively uniformly sized nuts throughout the tree's canopy. In addition to the foregoing, the nut of the new almond also appears to have good processing and shipping qualities.

The 'Buralmondthree' almond tree bears nuts that are typically ripe for commercial harvesting and hulling on approximately August 12 to August 20 under the ecological conditions prevailing in the San Joaquin Valley of central California. In relative comparison to the 'Nonpareil' almond tree, which is the closest known comparator variety, the new variety of almond tree is self-fertile ('Nonpareil' is not self-fertile). Additionally, the 'Buralmondthree' exhibits a well-sealed shell, which provides more protection from insect damage than the 'Nonpareil' (nonpatented). In comparison to the seed parent 'Tuono' (non-patented), the current variety blooms 2 to 3 days or more before and produces larger kernels. In comparison to the pollen parent 'Monterey', the current variety harvests ten days or earlier than the pollen parent variety, 'Monterey'. Additionally, the current variety is self-fertile, whereas 'Monterey' is self-incompatible.

BRIEF DESCRIPTION OF THE DRAWINGS

The accompanying drawings, which are provided, are color photographs of the new variety of Almond tree.

FIG. 1 depicts four (4) whole, shelled almond kernels, one of which is resting in a half shell, two (2) unshelled almonds, and one (1) unhulled/unshelled almond. Another almond (including the shell) is bisected in a horizontal plane and displays a cross-section of the shell, the inner seal, the kernel, its internal color, and the relative space between the kernel and the shell. Of the shelled and displayed almonds, three (3) kernels are exposed in a lateral view, which demonstrates the kernel veining, the relative shape, and the pellicle color. Further, one (1) kernel is set on its ventral edge and provides a view of the kernel from the dorsal perspective. Additionally, one (1) kernel is bisected, and placed on its apex, and further provides a view of the basal region. Inner and outer surfaces of removed hulls are also shown.

Figure 1:
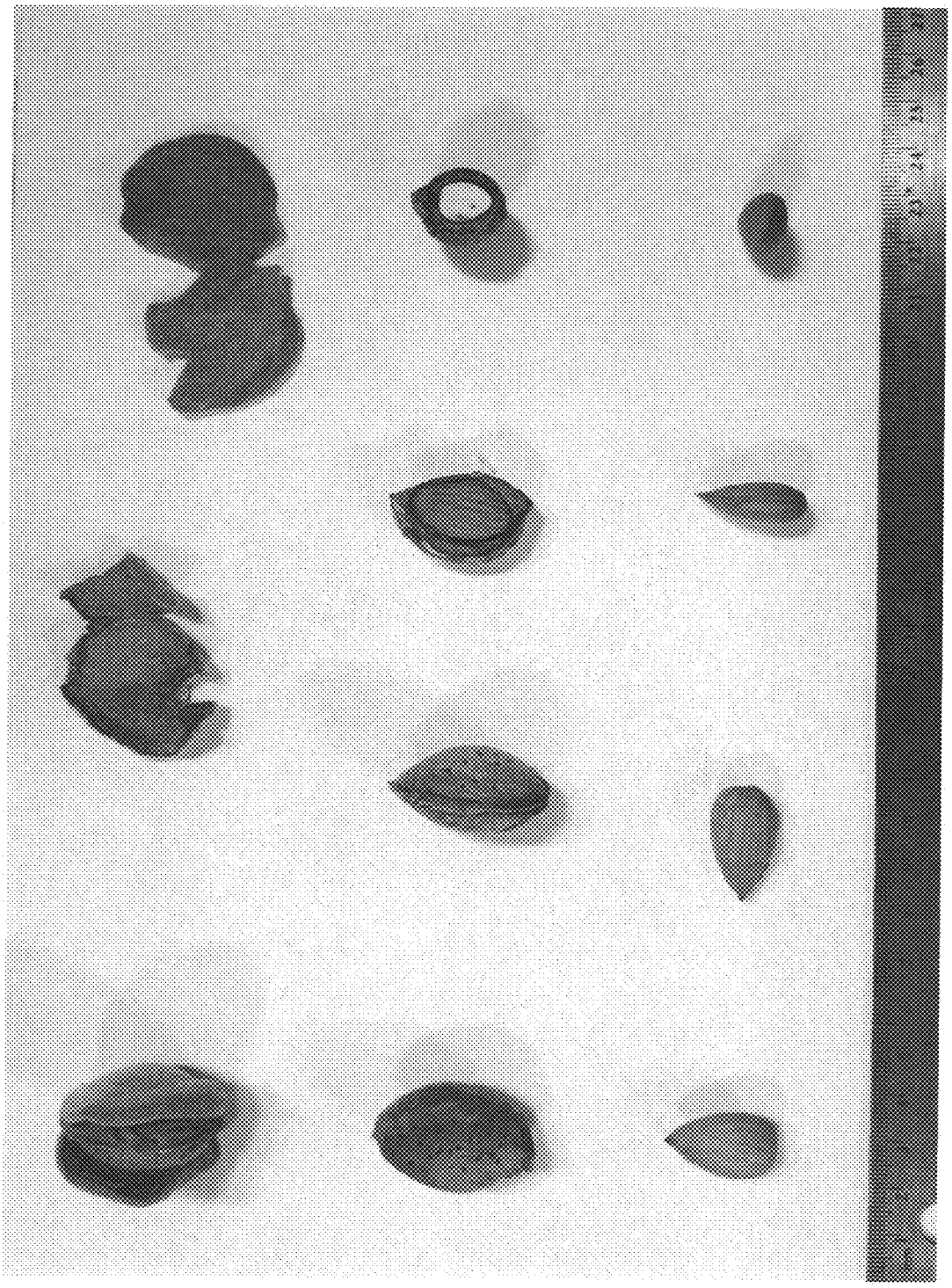
FIG. 1 depicts kernels, shells, and hulls of the new almond tree variety. The kernels, shells, and hulls are shown sufficiently matured for harvest.
Figure 2:
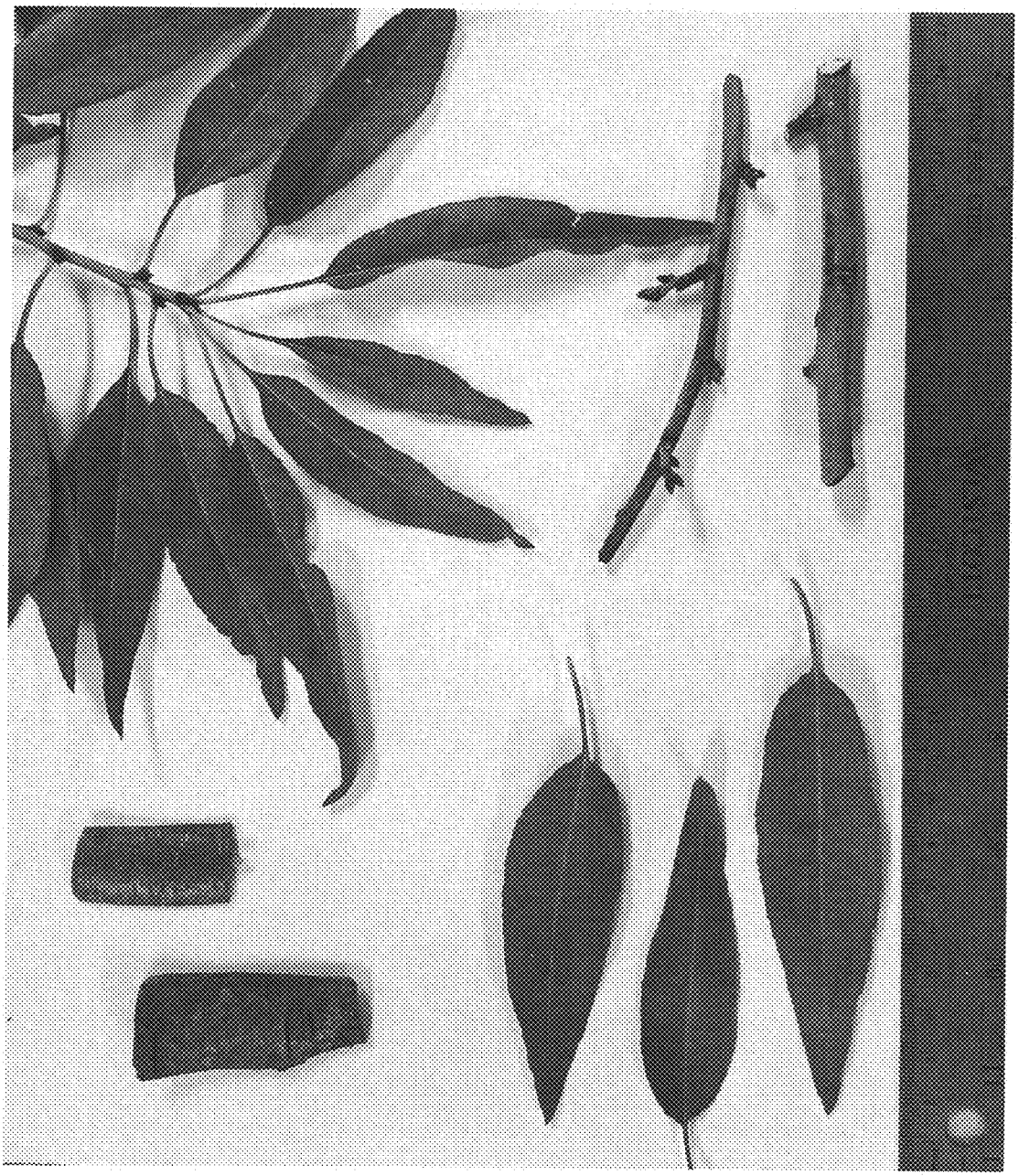
FIG. 2 depicts a twig bearing typical leaves, and several other leaves showing the dorsal and ventral coloration thereof. Samples of bark and other twigs are shown.

The colors in these photographs are as nearly true as is reasonably possible in a color representation of this type. Due to chemical development, processing and printing, the leaves and nuts depicted in these photographs may, or may not, be accurate when compared to the actual specimen. For this reason, future color references should be made to the color plates (Royal Horticultural Society, Fourth Edition, 2001), and descriptions provided, hereinafter.

NOT A COMMERCIAL WARRANTY

The following detailed description has been prepared to comply solely with the provisions of 35 U.S.C. § 112, and does not constitute a commercial warranty, (either express or implied), that the present variety will in the future display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of almond tree, the following has been observed during the 11th fruiting season, and under the ecological conditions prevailing at the orchards of the assignee which are located near the town of Fowler, county of Fresno, state of California. All major color code designations are by reference to The R.H.S. Colour Chart (Fourth Edition, 2001) provided by The Royal Horticultural Society of Great Britain. Common color names are also occasionally used.

Tree:

*Size.*—Generally considered medium in its growth pattern as compared to other common commercial almond cultivars. Height approximately 6.0-7.0 meters, width approximately 5.0-6.0 meters. Tree size can vary with commercial inputs, influence of rootstocks and soil fertility.

*Vigor.*—Considered vigorous. Tree height in the first growing season approximately 2.0 meters

*Form.*—Considered more upright than 'Nonpareil' (non-patented).

*Branching habit.*—Considered a prolific spur habit. Primary limb angles are approximately 55 to 65 degrees. The current variety generally produces long unbranched growth (apical dominance) if pruning or 'heading' is not practiced.

*Productivity.*—Productive. Typically produces more kilograms per tree than 'Nonpareil' (non-patented) when trees are grown under the same conditions. Productivity can vary with cultural practices and soil fertility.

*Bearing.*—Regular. Fruit set has been adequate during the previous years of observation, and the past ten years on both the original seedling and on subsequent asexually reproduced trees.

*Fertility.*—Self-fertile. Self-fertility has been confirmed in each of the previous 14 fruiting years.

*Density.*—Not considered a naturally dense canopy. New, current season growth tends to extend terminal buds which increase the fruit wood potential through spur development along limbs and branches. The current variety tends to have a more open canopy than Nonpareil (unpatented). Limb and canopy density can be significantly influenced by pruning (both heading and thinning cuts) and/or mechanical topping.

*Hardiness.*—The present tree was grown and evaluated in USDA Hardiness Zone 9. The calculated winter chilling requirements of the new tree is approximately 350 hours at a temperature below 7.0 degrees C. The present variety appears to be hardy under typical central San Joaquin Valley climatic conditions.

Trunk:

*Diameter.*—Approximately 28.5 centimeters (cm) in diameter when measured at a distance of approximately 15.24 cm above the soil level. This measurement was taken at the end of the 14th growing season.

*Bark texture.*—Considered moderately rough. Since bark development and coloration change with advancing tree age, this characteristic varies with the tree vigor, age, and regional conditions.

*Lenticels.*—Flat, oval lenticels are present. The lenticels range in size from approximately 4.0 millimeters (mm) to about 8.0 mm in width, and between about 1.0 and about 2.0 mm in height.

*Lenticel color.*—Considered an orange brown, (RHS Greyed-Orange Group 170 A).

*Bark coloration.*—Variable, but it is generally considered to be a greyed brown, (RHS Greyed-Brown Group 200 D).

Branches:

*Size.*—Considered medium for the variety.

*Diameter.*—Average as compared to other almond varieties. The branches have a diameter of about 16.0 cm when measured during the 14th year after grafting.

*Surface texture.*—Current season's and new growth is smooth.

*Current season shoots.*—Surface texture — Substantially glabrous.

*Feather of the shoot.*—Medium.

*Internode length.*—Approximately 2.0 cm.

*Color of mature branches.*—Grey-brown, (RHS Brown Group 199 C).

*Current seasons shoots.*—Color — Medium-light green, (RHS Yellow-Green Group 143 B). The color of new shoot tips will continue to darken to a greyed red as the growing season progresses (RHS Greyed-Red Group 178 B).

Leaves:

*Size.*—Considered medium-large for the species. Leaf measurements have been taken from vigorous, upright, current-season growth, at approximately mid-shoot. It should be understood that the leaf size is often influenced by prevailing growing conditions, quality of sunlight, and the location of the leaf within the tree canopy. For this reason, leaf sizes can vary significantly based upon the ambient and other cultural factors listed above.

*Leaf length.*—Approximately 95.0 to about 120.0 mm.

*Leaf width.*—Approximately 21.0 to about 28.0 mm.

*Leaf base-shape.*—The leaves generally exhibit oblique marginal symmetry relative to the leaf longitudinal axis.

*Leaf form.*—Lanceolate.

*Leaf tip form.*—Acuminate.

*Leaf color.*—Upper Leaf Surface — Dark green, (approximately RHS Green Group 137 D).

*Leaf color.*—Lower Leaf Surface — light to medium green, (approximately RHS Green Group 138 B).

*Leaf texture.*—Glabrous (both sides of leaf).

*Leaf venation.*—Pinnately veined.

*Mid-vein.*—Color — Considered a light, whiteish-green, (approximately RHS Green-White Group 157 B) in the early to mid-period of the growing season.

*Leaf margins.*—Generally not considered undulating when observed with adequate hydration. Form. — Considered crenate. Uniformity. — Considered generally uniform. Thickness. — Considered medium for the species.

*Leaf petioles.*—Form. — Considered canaliculated, and having a more pronounced trough when viewed from the dorsal aspect. The petiole margin is considered rounded when viewed from the ventral aspect. Size. — Considered very large for the species. Length. — About 24.0 to about 29.0 mm. Diameter. — About 1.5 to about 2.5 mm. Color. — Light yellow-green, (approximately RHS Yellow Green Group N142 A).

*Leaf glands.*—Size. — Considered small for the species; approximately 1.0 mm in length; and about 1.0 mm in height. Number. — Generally two glands per marginal side is found. Observations of more than two glands per marginal side are not uncommon. Type. — Glands located at the base of the leaf are predominantly globose in shape. Color. — Considered a medium brown, approximately (RHS Grey-Orange Group 165 C).

*Leaf stipules.*—Size. — Medium average for this variety (stipule length 4-5 mm, stipule diameter 6-7 mm). Number. — Typically two per leaf bud, and up to four or more per shoot tip. More apparent on terminal buds than lateral buds. Form. — Lanceolate in form, and having a serrated marginal edge. Color. — Pale Orange (approximately RHS Greyed Orange Group N167 C) when young, but graduating to a brown color, (approximately RHS Greyed-Orange Group 165 A) with advancing maturity and nearing senescence. The leaf stipules are generally considered to be early deciduous.

Flower buds:

*Hardiness.*—No winter injury (bud death) has been noted during the last several years of observation in the central San Joaquin Valley. The new variety of almond tree has not been intentionally subjected to drought, cold, or heat stress and, therefore, this information is not available.

*Flower bud.*—Size — Variable and dependent on the state of maturity. The flower buds as described were observed approximately seven (7) days prior to bloom. Shape — Long and narrow, being 15-20 mm long from the base of the stipules and starting 6-7 mm wide at the base, widening to only 10-12 mm in the middle, and tapering to 4-5 mm at the tip of the bud. Distribution — Equally on spurs and one year old shoots.

*Flower bud.*—Length — Approximately 14.0 mm.

*Flower bud.*—Diameter — Approximately 8.5 mm.

*Flower bud surface texture.*—Pubescent.

*Flower bud orientation.*—Considered appressed, but appear less so as the blossoms near opening.

*Bud scale color.*—Considered a Brownish purple (Approximately RHS Greyed-Orange Group 166 A).

Flowers:

*Date of first bloom.*—Observed on Feb. 17, 2018.

*Blooming time.*—Considered earlier than average in relative comparison to other commercial almond cultivars grown in the central San Joaquin Valley. The date of full bloom was observed on Feb. 24, 2018. Bloom dates can vary from season to season and accumulated chill hour requirements and also heat units received during the prebloom interval. The date of full bloom varies slightly with climatic conditions and prevailing cultural practices.

*Duration of bloom.*—Approximately 14 days or more. This particular characteristic varies slightly with the prevailing climatic conditions.

*Flower class.*—Considered a perfect flower, complete and perigynous.

*Flower type.*—The variety is considered to have a showy type flower.

*Flower size.*—Considered medium to small for the species. The flower diameter at full bloom is approximately 28.0 to 32.0 mm. Flower height at full bloom, is approximately 17.0 to 20.0 mm.

*Bloom quantity.*—Considered abundant (14.2 average flowers per 30 cm length of branch).

*Flower bud frequency.*—Normally two to multiple flower buds appears per node/spur, occasionally one flower bud per node is observed.

*Petal size.*—Generally considered medium small for the species. Petal Length. — Approximately 14.0 to 16.0 mm. Petal Width. — Approximately 14.0 to 16.0 mm.

*Petal form.*—Considered broadly obovatus.

*Petal count.*—Nearly always 5.

*Petal texture.*—Glabrous (both sides of petal).

*Petal color.*—Considered a dull white at the popcorn stage, (RHS White Group N155 A).

*Fragrance.*—Slight (sweet, like honey).

*Petal claw.*—Form. — The claw is considered obovatus and is generally medium-small when compared to other varieties. Length. — Approximately 9.0-11.0 mm. Width. — Approximately 8.0 to 10.0 mm.

*Petal margins.*—Generally considered variable, from nearly smooth to moderately undulate.

*Petal apex.*—Generally, the petal margin is entire at tip.

*Flower pedicel.*—Length. — Considered medium-long with an approximate length of about 2.5 to about 4.0 mm. Diameter. — Approximately 2.0 mm. Color. — A medium brown, approximately (RHS Grey-Brown Group 199 A). Surface. — Glabrous.

*Floral nectaries.*—Color. — Considered a deep orange (approximately RHS Greyed-Orange Group 173 C).

*Calyx.*—Surface Texture. — Generally glabrous. Color. — A dull green, (approximately RHS Green Group 138 B).

*Sepals.*—Surface Texture. — The surface has a short, fine pubescent texture. Number. — Five (5) sepals. Size. — Average and ovatus in form. Sepal Length. — Approximately 5.0 to 6.0 mm. Sepal Width. — Approximately 5.0 to 6.0 mm. Sepal Shape. — Generally obovate. Sepal Margin. — Considered smooth and entire. Sepal Color. — A dull, magenta, (approximately RHS Greyed-Red Group 181 B).

*Anthers.*—General. — Average in size (35-37 anthers per flower with an average size of 0.5-1.0 mm per anther) with the stigma above the anthers. Color. — Red to Greenish Yellow when viewed dorsally and prior to dehiscence, (approximately RHS Yellow-Group 144 C). Pollen Production. — Pollen is abundant and has a yellow color, (approximately RHS Yellow-Orange Group 12 C).

*Fertility.*—Self-fertile.

*Filaments.*—Size. — Approximately 8.0 to 11.0 mm in length. Approximately 0.5 to 0.7 mm in width. Color. — Considered white (RHS White Group N155 B).

*Pistil.*—Number. — Usually one, and only rarely more than one. Generally — Medium in size. Length. — Approximately 11.0 to about 12.5 millimeters in length including the ovary. Color. — Considered a very pale green (approximately RHS Yellow-Green Group 150 A). Surface Texture. — The variety has a long pubescent pistil.

Nut crop:

*Productivity.*—Very productive. Variety is very precocious.

*Maturity when described.*—Ripe for commercial harvest condition.

*Date of first harvest.*—Approximately Aug. 15, 2017. The date of harvest can vary slightly with the prevailing climatic conditions, crop load, rootstock and the current cultural practices. Generally nuts are mature after 'Nonpareil' (non-patented).

*Distribution.*—Almonds are generally well clustered on bearing spurs spread evenly throughout the bearing canopy.

*Tenacity.*—Shell adhesion is firm until harvest. Nut removal is thorough at harvest.

Hull:

*Surface.*—Relatively smooth prior to and after harvest. Hull is covered with short fine pubescence.

*Form.*—Elliptical.

*Thickness.*—Considered very thin at time of kernel maturity. Very little mesocarp pulp or fibers adhere to the shell.

*Flesh.*—Leathery, becoming brittle when dry.

*Suture.*—Considered smooth.

*Color.*—A dull tan color. Exterior color (Approximately RHS Greyed-Green Group 193 A). Internal hull color a greyish orange (Approximately RHS Greyed-Orange Group 165 C).

*Typical weight.*—Approximately 5.0 grams. This characteristic is quite dependent upon the prevailing cultural practices, and therefore is not particularly distinctive of the new variety.

*Dehiscence.*—Very open and widely flaring with clean separation at the suture and throughout the mesocarp.

*Adherence.*—Very weak and easily removed in the hulling process.

Shell:

*Size.*—Large. Approximate length 30.0-38.0 mm. Width approximately 18.0-25.0 mm. Thickness approximately 14.0-19.5 mm.

*Color.*—Exterior color a brownish white (RHS Greyed-Orange Group 164 D). Inner shell color a pale orange (RHS Greyed-Orange 165 C).

*Surface.*—The surface of the shell nearer the suture exhibits shallow angled furrows ending at suture. The remaining shell surface is covered with pitting. The inner seal of the shell is quite smooth. Sufficient space exists between the exterior of the kernel and the shell inner seal to allow removal of the nut from the endocarp during the shelling process. The shell is sound and durable, but can be opened by hand.

*Apex.*—Acuminate. Length, approximately 2.0-3.0 mm.

*Base.*—Slightly oblique toward the ventral side.

*Suture.*—A wing/fin extends away from the shell at the suture and is present from base to apex. Approximately, 2.0-3.0 mm in width. Approximately, 1.0-2.0 mm in thickness. Suture is totally sealed and resistant to ant damage.

*Stem scar/hilum.*—Relatively wide. Approximately 5.0-6.5 mm in width. 3.0-4.0 mm in height.

Kernel:

*Size.*—Large. Approximately, 22.0-26.0 mm in length. Approximately, 13.0-16.5 mm in width. Approximately, 7.0-10.0 mm in thickness. Approximate weight 1.6 grams. The conditions under which almonds trees are cultured can influence individual kernel size and weight both positively and negatively. Additionally, the number of almond fruits attached to each spur can be influential in kernel size.

*Form.*—Ovatus to slightly elliptical.

*Shape.*—Relatively flat in kernel thickness. Similar to 'Nonpareil' (unpatented) with more thickness. Base is generally rounded to slightly oblique to the dorsal side. Apex concludes in a short fine point approximately 1.0 millimeter in length.

*Surface texture.*—Relatively smooth with slight and gentle ribbing noted between the kernel veining. Similar to 'Nonpareil' (nonpatented).

*Pellicle.*—Tenacious to the kernel meats. Medium to thin relative to current commercial almond varieties. Very light pubescence.

*Color.*—Considered a light golden brown approximately (RHS Greyed-Orange Group 167 B) to a slightly darker (RHS Greyed-Orange Group 165 B). Kernel color can vary with growing conditions, tree age, and irrigation practices.

*Double kernels.*—The variety exhibits percentage of double (or twin) kernels. The percentage of double kernels is typically less than 15%.

*Flavor.*—Sweet, rich with an essence of marzipan.

*Quality.*—Very high quality with low percentages of kernel defects or ant damage.

*Use.*—Both as a shelled and in-shell almond for both local and export markets.

*Keeping quality.*—Kernels have been stored for one year and two year studies with good flavor, low defects, rancidification or kernel discoloration.

*Shipping quality.*—Very good. Similar to other commercial almond varieties.

*Resistance to insects and disease.*—The present variety has exhibited a firm, durable and well-sealed suture that has resulted in virtually no damage from ants and Navel Orange Worm (*Amylose transitella*) gaining access to and feeding on the almond kernels unlike 'Nonpareil' (unpatented) and other existing, open sutured varieties. The current variety has exhibited a lower susceptibility to the fungus pathogen *Rhizopus stolonifer* (commonly known as 'hull rot', 'black mold' or 'bread mold') than 'Nonpareil' (unpatented) which is the current commercial standard almond variety.

Although the new variety of almond tree possesses the described characteristics when grown under the ecological conditions prevailing near Fowler, Calif., in the Central part of the San Joaquin Valley of California, it should be understood that variations of the usual magnitude, and characteristics incident to changes in growing conditions, fertilization, nutrition, pruning, pest control, frost, climatic variables and changes in horticultural management are to be expected.

Having thus described and illustrated our new variety of almond tree, what I claim is new and desire to secure by plant Letters Patent is:

1. A new and distinct variety of almond tree, substantially as illustrated and described, and which is characterized principally as to novelty in exhibiting self-fertility; high productivity; very high quality light colored nuts; a firm, durable and well-sealed suture that results in reduced damage from some the common insect pests in almonds; increased resistance to *Rhizopus stollinifer* when compared to 'Nonpareil' (nonpatented); and which is mature for harvesting approximately August 15th to August 25th under the ecological conditions prevailing in the San Joaquin Valley of Central California.

* * * * *